(12) United States Patent
Hunter et al.

(10) Patent No.: US 6,652,586 B2
(45) Date of Patent: Nov. 25, 2003

(54) PROSTHETIC DEVICES EMPLOYING OXIDIZED ZIRCONIUM AND OTHER ABRASION RESISTANT SURFACES CONTACTING SURFACES OF CROSS-LINKED POLYETHYLENE

(75) Inventors: Gordon Hunter, Memphis, TN (US); Shilesh C. Jani, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1 day.

(21) Appl. No.: 09/908,520

(22) Filed: Jul. 18, 2001

(65) Prior Publication Data

US 2003/0028254 A1 Feb. 6, 2003

(51) Int. Cl.⁷ .................................................. A61F 2/30
(52) U.S. Cl. ................... 623/18.11; 623/20.14; 623/22.17; 623/22.24
(58) Field of Search .................. 623/18.11, 20.14, 623/20.22, 22.11, 22.15, 22.17, 22.24

(56) References Cited

U.S. PATENT DOCUMENTS

| | | |
|---|---|---|
| 5,037,438 A | 8/1991 | Davidson |
| 5,152,794 A | 10/1992 | Davidson |
| 5,180,394 A | 1/1993 | Davidson |
| 5,370,694 A | 12/1994 | Davidson |
| 5,414,049 A * | 5/1995 | Sun et al. |
| 5,879,400 A * | 3/1999 | Merrill et al. |
| 6,017,975 A * | 1/2000 | Saum et al. |
| 6,165,220 A * | 12/2000 | McKellop et al. |
| 6,168,626 B1 * | 1/2001 | Hyon et al. |
| 6,228,900 B1 * | 5/2001 | Shen et al. |
| 6,281,264 B1 * | 8/2001 | Salovey et al. |
| 6,316,158 B1 * | 11/2001 | Saum et al. |
| 6,447,550 B1 * | 9/2002 | Hunter et al. |

FOREIGN PATENT DOCUMENTS

| | | | |
|---|---|---|---|
| EP | 722973 A1 | * | 7/1996 |
| EP | 729981 A1 | * | 9/1996 |
| EP | 737481 A1 | * | 10/1996 |
| WO | WO 98/01085 | * | 1/1998 |
| WO | WO 98/14223 | * | 4/1998 |
| WO | WO 98/16258 | * | 4/1998 |

* cited by examiner

Primary Examiner—Ralph A. Lewis
(74) Attorney, Agent, or Firm—Fulbright & Jaworski L.L.P.

(57) ABSTRACT

Orthopedic implants which includes the components of zirconium or zirconium-based alloys having surfaces coated with oxidized zirconium or alternatively, other orthopedic implants comprising abrasion resistant surfaces contacting surfaces of cross-linked polyethylene are disclosed. Such implants provide low friction, highly wear resistant coatings especially useful in artificial joints, such as hip joints, knee joints, elbows, etc., but also useful in other implant devices as well.

34 Claims, 1 Drawing Sheet

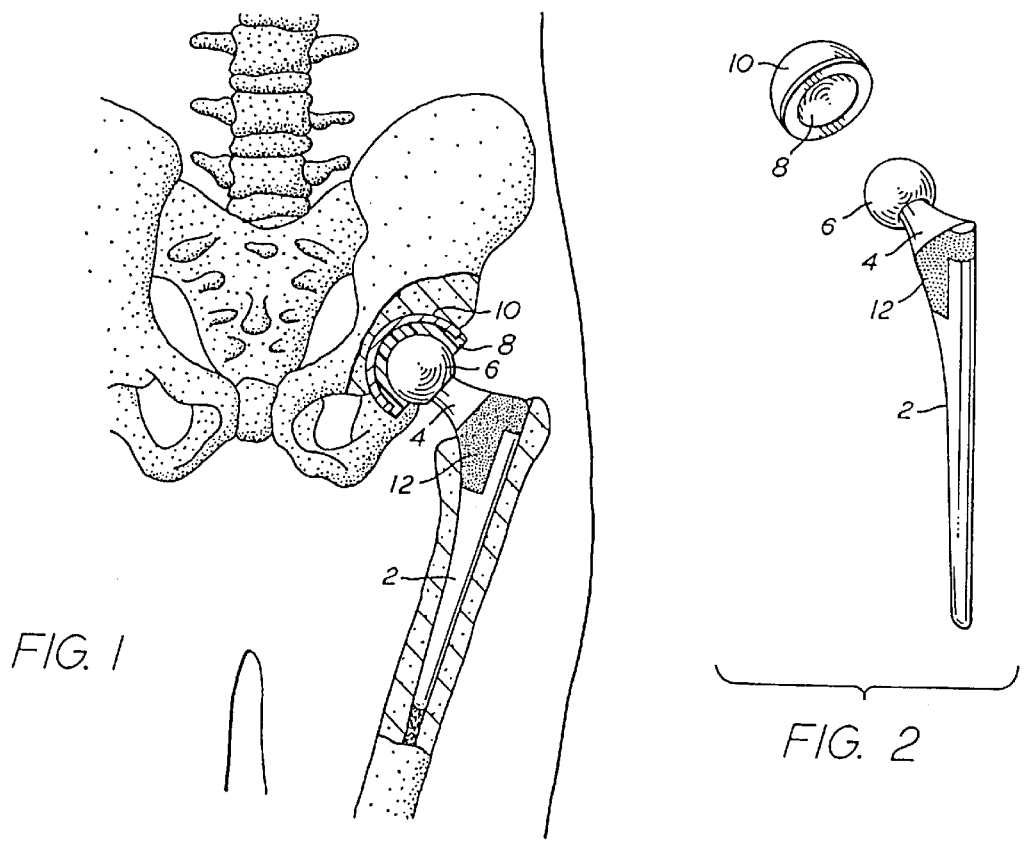
FIG. 1
FIG. 2
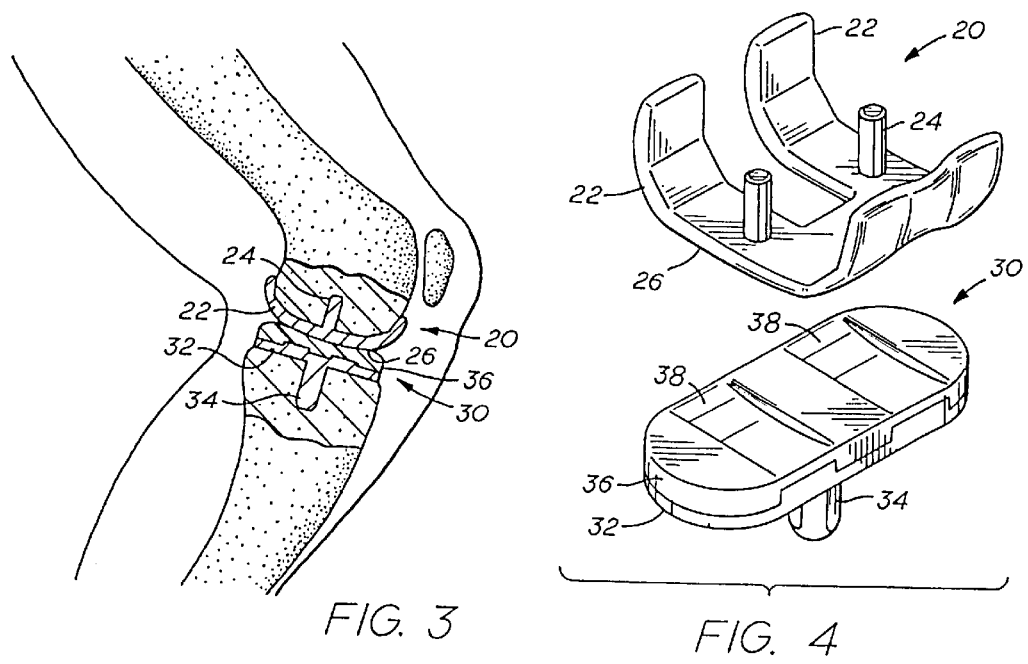
FIG. 3
FIG. 4

PROSTHETIC DEVICES EMPLOYING OXIDIZED ZIRCONIUM AND OTHER ABRASION RESISTANT SURFACES CONTACTING SURFACES OF CROSS-LINKED POLYETHYLENE

BACKGROUND OF THE INVENTION

This invention relates to metallic implants with load bearing surfaces coated with a thin, dense, low friction, highly wear-resistant, uniformly thick coating of oxidized zirconium. This invention also relates generally to metallic implants with load bearing, abrasion resistant surfaces. In the present invention, the load bearing oxidized zirconium surfaces or abrasion resistant surfaces contact counter bearing surfaces of cross-linked polyethylene (XLPE). XLPE has superior wear characteristics compared with other conventional polymer materials used in prostheses. Oxidized zirconium has thermal conductivity characteristics that are particularly advantageous when used in a prosthetic device in which it articulates against XLPE. The unique advantages of oxidized zirconium and abrasion resistant surfaces in combination with those of XLPE result in a synergy which allows one to accentuate the superior properties of XLPE as a counter bearing surface, resulting in a superior prosthetic device.

Historically prostheses of articulating surfaces were constructed of materials of differing hardness for the contacting surfaces. By having one "yielding" surface, such prior art devices eventually form an optimal fit, i.e., a tight tolerance, whereby galling, fretting, and other erosive phenomena are minimized, resulting in longer-lasting prosthetic devices. An example of these early-generation devices is the femoral head of a hip-stem prosthesis which engages a counter-bearing surface in an acetabular cup which is often made of a softer material such as ultra-high molecular weight polyethylene. However, use of contacting surfaces of different hardness is not a perfect solution. The softer surface is, by nature sacrificial; it will eventually fail, its main virtue is the realization of an overall increase in the useful life of the prostheses. Additionally, fretting of the softer surface results in debris that may have deleterious effects on the health on the patient.

The invention described herein is a particular type of ceramic-on-polymer prosthesis. Its unique compositional properties affords the traditional advantages of ceramic-on-polymer systems while avoiding their major disadvantage.

The invention overcomes the major disadvantage generally inherent in prosthetic devices having hard surfaces articulating against soft surfaces. The basic technology upon which the improvement described herein is based, is described in U.S. Pat. No. 5,037,438 to Davidson and to commonly assigned, copending application Ser. No. 09/381,217, filed Nov. 24, 1999 now U.S. Pat. No. 6,447,550 of Hunter, et al., both of which are fully incorporated by reference herein.

The longevity of medical implant devices is of prime importance as it is desirable that the implant should function for the complete lifetime of a patient. This is particularly true if the patient is young and the number of surgical revisions is to be kept to a minimum and preferably zero. To this end, orthopedic implant materials should preferably combine high strength, corrosion resistance and tissue compatibility. One of the variables affecting the longevity of load-bearing implants such as hip-joint implants is the rate of wear of the articulating surfaces and long-term effects of metal ion release. A typical hip-joint prosthesis includes a stem, a femoral head and an acetabular cup against which the femoral head articulates. Wear of either or both of the articulating surfaces results in an increasing level of wear particulates and "play" between the femoral head and the cup against which it articulates. Wear debris can contribute to adverse tissue reaction leading to bone resorption, and ultimately the joint must be replaced.

The rate of wear of the acetabular cup and the femoral head surfaces of artificial hips is dependent upon a number of factors which include the relative hardness and surface finish of the materials which constitute the femoral head and the acetabular cup, the frictional coefficient between the materials of the cup and head, the load applied and the stresses generated at the articulating surfaces. The most common material combinations currently used in the fabrication of hip-joint implants include femoral heads of cobalt, titanium, or zirconium alloys articulating against acetabular cups lined with organic polymers or composites of such polymers including, for instance, ultra-high molecular weight polyethylene (UHMWPE) and femoral heads of polished alumina in combination with acetabular cups lined with an organic polymer or composite or made of polished alumina.

Of the factors which influence the rate of wear of conventional hip-joint implants, the most significant are patient weight and activity level. Additionally, heat generated by friction in the normal use of the implant has been shown to cause accelerated creep and wear of the polyethylene cup. Furthermore, there is a correlation between the frictional moment which transfers torque loading to the cup and the frictional coefficient between the femoral head and the surface of the acetabular cup against which the head articulates. Cup torque has been associated with cup loosening. Thus, in general, the higher the coefficient of friction for a given load, the higher the level of torque generated. Ceramic bearing surfaces have been shown to produce significantly lower levels of frictional torque. It is also noteworthy that two of the three commonly used hip-joint systems as indicated above include a metallic femoral head articulating against an ultra high molecular weight polyethylene (UHMWPE) liner inside the acetabular cup. UHMWPE, being a polymeric material, is more susceptible to creep at higher temperatures than the commonly used metal alloys or ceramics due to its relatively lower melting point and is consequently more susceptible to wear than the alloys or ceramics.

The original impetus for the inclusion of surfaces such as UHMWPE was that they would act sacrificially; they would fail slowly and fail before the harder surface, allowing for an overall extension of the useful life of the device. Additionally, polyethylene was thought to absorb shock much better than harder surfaces, thereby simulating the effect of real cartilage. While the advance in the art which was realized by the use of oxidized zirconium surfaces articulating against UHMWPE surfaces was a lessening of wear and cup loosening between the surface of the metallic component and the UHMWPE, the problem was not completely eliminated. Thus, the instant invention represents another advancement in the art, namely, a further improvement in wear and a simultaneous significant improvement of the creep problem associated with the prior art prostheses comprising polyethylene articulating against harder surfaces.

It has also been found that metal prostheses are not completely inert in the body. Body fluids act upon the metals causing them to slowly corrode by an ionization process thereby releasing metal ions into the body. Metal ion release from the prosthesis is also related to the articulation and rate of wear of load bearing surfaces because, as may be expected, when a metallic femoral head, for instance, is articulated against UHMWPE, the passive oxide film which forms on the femoral head is constantly removed. The repassivation process constantly releases metal ions during this process. Furthermore, the presence of third-body wear (cement or bone debris) accelerates this process and micro-fretted metal particles can increase friction. Consequently, the UHMWPE liner inside the acetabular cup, against which the femoral head articulates, is subjected to accelerated levels of creep, wear, and torque. A reduction in these deleterious effects will also improve the problem of metal ion release.

A number of attempts to correct these problems were the subject of much of the early work in this area. U.S. Pat. No. 4,145,764 to Suzuki taught a metal prosthesis plasma sprayed with a bonding agent which is in turn covered with a porous ceramic coating which would allow the in-growth of bone spicules into the pores. However, the Suzuki patent did not address the issue of friction or wear of orthopedic implant bearing surfaces but confined itself to the single issue of the biocompatibility of metal prostheses and did not address the issue of dimensional changes that occur when applying such a coating. U.S. Pat. No. 3,677,795 to Bokros is directed to the application of a carbide coating over a metallic prosthetic device. The method is said to produce a prosthetic device which has "excellent compatibility with body tissue and is non-thrombogenic". However, Bokros does not address the issues of friction, heating, creep and wear of orthopedic implant bearing surfaces, or changes induced in the mechanical properties of the underlying metal due to this high-temperature treatment.

The aforementioned failings of the prior art were addressed in part by Davidson in U.S. Pat. No. 5,037,438. In the '438 patent, Davidson teaches a zirconium or zirconium-containing metal alloy prosthesis coated via in-situ oxidation with a surface of blue-black or black oxidized zirconium which articulates against an organic polymer or polymer-based composite. The oxidized zirconium coating provides the prosthesis with a thin, dense, low friction, wear resistant, biocompatible surface ideally suited for use on articulating surfaces of joint prostheses wherein a surface or surfaces of the joint articulates, translates or rotates against mating joint surfaces. The oxidized zirconium coating described the '438 patent may therefore be usefully employed on the femoral heads or inside surfaces of acetabular cups of hip-joint implants or on the articulating surfaces of other types of prostheses, such as knee joints. Notably, the oxidized zirconium coating of the '438 patent was a specific type of oxidized zirconium. Oxidized zirconium presents itself in many forms, among them are white, beige, and blue-black. The white variety is particularly disfavored in the present application, as it tends to separate and break off of the substrate. Conventional oxidized zirconium surfaces formed, for example, by simple air oxidation will not be of the blue-black or black variety and will not possess the superior properties of the same which are recited in the '438 patent. The most important of these properties high hardness, low friction that results from the presence of the surface oxide.

The specific blue-black or black oxidized zirconium coatings of the '438 patent were known in the art of mechanical bearings, having been described in U.S. Pat. No. 2,987,352, which teaches a 700–1100° F. oxidation method to produce the specific blue-black or blue oxidized zirconium coating.

A later issuing patent to Haygarth (U.S. Pat. No. 4,671,824) teaches an alternative, salt-bath method to produce the desired coating. The blue-black or black oxidized zirconium of the instant invention possessing the necessary properties is primarily monoclinic crystal structure. This has been characterized by Hunter et al. (Hunter, G, et al., Mat. Res. Symp. Proc., (1999), 550, 337).

The introduction of XLPE as a counter bearing surface in articulating prostheses was another unrelated attempt to address the problem of the relatively short service life of the UHMWPE component. Cross-linking of UHMWPE forms covalent bonds between polymer chains which retard the process of wear through the internal reinforcement of the individual polymer chains. However, XLPE is not without problems. The advantages of XLPE over other forms of polyethylene diminish as the roughness of the counter bearing surface increases and the operating temperature of device increases. Thus, a counter bearing surface, which possesses properties that prevent or improve the aforementioned conditions, would accentuate the advantages of XLPE over conventional forms of polyethylene. Additionally, there is anecdotal evidence that the improvement of wear characteristics comes at a cost of greater susceptibility to creep, particularly at elevated temperatures.

XLPE devices have exhibited other deficiencies, with which the prior art has largely been concerned about. Free radicals formed during irradiation, however, can exist indefinitely if termination by cross-linking or other forms of recombination do not occur. Furthermore, reacted intermediates are continuously formed and decayed. Exposure of these free radical species at any time (e.g., during irradiation, shelf-aging, or in vivo aging) to molecular oxygen or any other reactive oxidizing agent can result in their oxidation. Extensive oxidation leads to a reduction in molecular weight, and subsequent changes in physical properties, including wear resistance. Many attempts have been made to improve the characteristics of XLPE. These attempts include radiation induced cross linked polyethylene (See U.S. Pat. Nos. 5,728,748; 5,650,485; 5,543,471; 5,414,049; and 5,449,745 to Howmedica; Johnson & Johnson's EP 0737481 A1, see also Hamilton, J. V. et al., Scientific Exhibit, 64$^{th}$ AAOS Meeting, February 1997; Hamilton, J. V. et al., Trans 43$^{rd}$ ORS, 782, 1997; Biomet's World Patent Application No. 97/29787; see also Oonishi, H. et al., Radiat. Phys. Chem., 39(6), 495, 1992; Oonishi, H. et al., Mat. Sci: Materials in Medicine, 7, 753-63, 1966, Oonishi, H. et al., J. Mat. Sci: Materials in Medicine, 8, 11–18, 1997; U.S. Pat. No. 5,879,400; World Patent Application WO 98/01085; U.S. Pat. No. 6,165,220; EP 0729981 A1; U.S. Pat. Nos. 6,017,975; and 6,228,900, for chemical cross-linking of polyethylene (See EP 0722973 A1)).

In the present invention, the improvement in the performance of XLPE is realized not through improvements in the XLPE composition itself, but rather through the use of oxidized zirconium or other abrasion resistant surface as a counter bearing surface against which the XLPE component articulates. The advantages of the instant invention will be the preservation of the desirable properties of XLPE with a simultaneous elimination of some of its negative properties. The '438 patent did not contemplate and nowhere does it teach, the use of the oxidized zirconium surfaces directly contacting surfaces of XLPE. The inventors have discovered that the unique properties of oxidized zirconium accentuate the inherent advantages of XLPE as a counter bearing surface. The superior strength and hardness, low friction, wear resistance, thermal conductivity, and biocompatibility characteristics of the blue-black or black oxidized zirconium is sufficient in itself to considerably slow and possibly prevent the degradative wear processes to which the prosthetic devices of the prior art have been subject. An unapparent synergy is realized because the unique properties of oxidized zirconium serve to improve the performance of XLPE as a counter bearing surface. These unexpected advantages are also present, to a lesser degree, when other abrasion resistant surfaces are used.

The invention is directed to forming prosthetic devices of oxidized zirconium-on-XLPE, which represents a special species of oxidized zirconium-on-polymer devices, exhibiting even longer overall useful service life relative to conventional prostheses materials-on-UHMWPE. This is due not only to the advantages which inure upon the substitution of oxidized zirconium for conventional prosthesis materials, but also from the synergistic improvement in XLPE performance that is seen when XLPE articulates against oxidized zirconium. The invention is not limited to prostheses formed of zirconium or zirconium alloy. The prostheses substrate may itself be a composite material, only requiring that zirconium or zirconium alloy be present in the substrate layer immediately adjacent to the surface upon which the oxidized zirconium coating is to be formed.

SUMMARY OF THE INVENTION

As used herein, "a" or "an" may mean one or more. As used herein in the claim(s), when used in conjunction with the word "comprising", the words "a" or "an" may mean one or more than one. As used herein "another" may mean at least a second or more.

As used herein, "abrasion resistant surface" is defined as a material surface having a greater hardness than the underlying substrate. When used in reference to the underlying substrate material, it is synonymous with "surface hardened". An oxidized zirconium surface is one example of an abrasion resistant surface. Others include, but are not limited to substrates coated with ceramic materials.

As used herein, "base material" is defined as the material upon which a layer of oxidized zirconium is to be formed. It may be homogeneous, consisting of a single phase material, or it may be heterogeneous, consisting of a composite material of one or more substrate layers.

As used herein, the term "contacting surface" refers to any two surfaces of the prosthetic device or medical implant that contact one another in either a load bearing (articulating) or non-load bearing (non-articulating) manner.

As used herein, "substrate layer" is defined as a distinct chemical region or domain within the base material. A substrate layer may or may not be comprised of zirconium or zirconium alloy.

As used herein, "zirconium alloy" is defined as any metal alloy containing zirconium in any amount greater than zero. Thus, an alloy in which zirconium is a minor constituent is considered a "zirconium alloy" herein.

The following discussion contains illustration and examples of preferred embodiments for practicing the present invention. However, they are not limiting examples. Other examples and methods are possible in practicing the present invention and would be apparent to one of skill in the art upon reading the present disclosure.

In one embodiment of the present invention, a knee prosthesis for implantation in a patient comprises a prosthesis body formed of zirconium or zirconium alloy. The prosthesis body has an implant portion for inserting into the body tissue of a patient, a bearing surface having at least one condyle on the prosthesis body, a tibial component comprised of cross-linked polyethylene and having a surface adapted to cooperate with the bearing surface, and a thin coating of blue-black or black oxidized zirconium directly on the bearing surface of the condyle portion.

In specific embodiments of a knee prosthesis, the thin blue-black or black oxidized zirconium coating is from about 1 to about 20 microns thick. Preferably, the blue-black or black oxidized zirconium coating is from about 1 to about 5 microns thick. In a further embodiment, the knee prosthesis has an implant portion of the prosthesis body that has, at least in part, an irregular surface structure adapted to accommodate tissue in-growth on a portion of the prosthesis body. In a specific embodiment of the irregular surface structure prosthesis, the irregular surface structure can have zirconium or zirconium alloy beads attached to the outer surface of the prosthesis body, with at least a portion of the surface of the beads being oxidized to blue-black or black oxidized zirconium. In another embodiment of the irregular surface structure prosthesis, the irregular surface structure can have zirconium or zirconium alloy wire mesh connected to the outer surface of the prosthesis body, wherein at least a portion of the surface of the mesh is oxidized to blue-black or black oxidized zirconium.

In another embodiment of the invention, a hip prosthesis for implantation in a patient includes a hip prosthesis body for implantation into a femur which has a head portion formed at least in part of zirconium or zirconium alloy, a bearing surface on the head portion of the prosthesis body, and an acetabular cup having an inner surface comprising cross-linked polyethylene. A cooperating surface is adapted to engage and articulate with the bearing surface on the head portion. A thin coating of blue-black or black oxidized zirconium is formed directly on the exposed bearing surface of the head portion.

In a specific embodiment of the hip prosthesis, the thin blue-black or black oxidized zirconium coating is from about 1 to about 20 microns thick. Preferably, the thin blue-black or black oxidized zirconium coating is from about 1 to about 5 microns thick. In another embodiment, the prosthesis body further includes an irregular surface structure adapted to accommodate tissue in-growth on a portion of the prosthesis body. In a specific embodiment of the irregular surface structure prosthesis, the irregular surface structure is formed of zirconium or zirconium alloy beads connected to the outer surface of the prosthesis body. At least a portion of the surface of the beads is oxidized to blue-black or black oxidized zirconium. In yet another embodiment of the irregular surface structure prosthesis, the irregular surface structure is formed of zirconium or zirconium alloy wire mesh connected to the outer surface of the prosthesis body. At least a portion of the surface of the mesh is oxidized to blue-black or black oxidized zirconium.

In another embodiment of the invention, a prosthesis for implantation in a patient includes a prosthesis body formed at least in part of zirconium or zirconium alloy. The prosthesis body includes an implant portion for insertion into the body tissue of the patient, a bearing surface on the prosthesis body, the bearing surface being sized and shaped to engage and articulate with a second bearing surface on another prosthesis portion. The second bearing surface is formed of a cross-linked polyethylene. The prosthesis also includes a coating of blue-black or black oxidized zirconium from about 1 to about 5 microns in thickness on the bearing surface.

In a specific embodiment, the prosthesis body is a hip joint having a head portion as a bearing surface and another prosthesis portion is an acetabular cup, the head portion being adapted to cooperate with the inner surface of the acetabular cup, and the inner surface of the acetabular cup is also the second bearing surface. In another embodiment the prosthesis body is a knee joint and the bearing surface of the prosthesis body includes at least one condyle, and another prosthesis portion including a tibial component, with at least one condyle being adapted to cooperate with the tibial component. In a specific embodiment, the prosthesis body has an irregular surface structure adapted to accommodate tissue in-growth on at least a portion of the prosthesis body. In another embodiment of the irregular surface structure prosthesis, the irregular surface structure is formed of zirconium or zirconium alloy beads connected to the outer surface of the prosthesis body, where at least a portion of the surface of the beads is oxidized to blue-black or black oxidized zirconium. In a specific embodiment, the irregular surface structure prosthesis has an irregular surface structure formed of zirconium or zirconium alloy wire mesh connected to the outer surface of the prosthesis body, wherein at least a portion of the surface of the mesh is oxidized to blue-black or black oxidized zirconium.

In another embodiment, the invention is directed towards a prosthesis for implantation in a patient which includes a prosthesis body formed at least in part of zirconium or zirconium alloy, the prosthesis body includes an implant portion for inserting into the body tissue of the patient, a bearing surface on the prosthesis body, a counter-bearing surface formed of cross-linked polyethylene and adapted to cooperate with the bearing surface and, a thin coating of blue-black or black oxidized zirconium directly on the bearing surface.

In a specific embodiment, the thin blue-black or black oxidized zirconium coating is from about 1 to about 20 microns thick. Preferably, the thin blue-black or black oxidized zirconium coating is from about 1 to about 5 microns thick. In another embodiment, the implant portion of the prosthesis body further includes an irregular surface structure adapted to accommodate tissue in-growth on a portion of the prosthesis body. In a specific embodiment of the irregular surface structure prosthesis, the irregular surface structure is formed at least in part of zirconium or zirconium alloy beads attached to the outer surface of the prosthesis body, with at least a portion of the surface of the beads being oxidized to blue-black or black oxidized zirconium. In yet another specific embodiment of the irregular surface structure, the irregular surface structure is formed of zirconium or zirconium alloy wire mesh connected to the outer surface of the prosthesis body, with at least a portion of the surface of the mesh being oxidized to blue-black or black oxidized zirconium.

In another embodiment, a prosthesis for implantation in a patient, includes a prosthesis body comprising a substrate material. The prosthesis body includes an implant portion for inserting into the body tissue of the patient, a bearing surface on the prosthesis body formed of any abrasion resistant surface, and a counter-bearing surface formed of cross-linked polyethylene and adapted to cooperate with the bearing surface. In a specific embodiment, the implant portion of the prosthesis body further includes an irregular surface structure adapted to accommodate tissue in-growth on a portion of the prosthesis body. In a specific embodiment of the irregular surface structure prosthesis, the irregular surface structure has beads attached to the outer surface of the prosthesis body, with at least a portion of the surface of the beads is oxidized to blue-black or black oxidized zirconium. In another specific embodiment of the irregular surface structure prosthesis, the irregular surface structure is formed wire mesh connected to the outer surface of the prosthesis body, with at least a portion of the surface of the mesh is oxidized to blue-black or black oxidized zirconium.

DESCRIPTION OF THE DRAWINGS

FIG. 1 is a schematic diagram depicting a hip joint prosthesis in position.

FIG. 2 is a schematic diagram showing a typical hip joint prosthesis.

FIG. 3 is a schematic diagram of a knee joint prosthesis in place.

FIG. 4 is a schematic diagram of the parts of a typical knee joint.

DETAILED DESCRIPTION OF THE INVENTION

The present invention provides low friction, wear and creep resistant, articulating, interfacial bearing surfaces for prosthetic devices. Preferably, the invention provides for a prosthetic device in which one contacting surface is formed of blue-black or black oxidized zirconium and another contacting surface is formed of XLPE. Alternatively, one contacting surface is formed of an abrasion resistant material and another contacting surface is XLPE.

Oxidized zirconium presents itself in many forms, among them are white, beige, and blue-black. The white variety is particularly disfavored in the present application, as it tends to separate and break off of the substrate readily. Conventional oxidized zirconium surfaces formed, for example, by simple air oxidation will not be of the blue-black or black variety.

The blue-black or black oxidized zirconium of the instant invention possessing the necessary properties is primarily monoclinic crystal structure and may include tetragonal zirconia. Its microstructure has been characterized by Hunter et. al. The specific blue-black or black oxidized zirconium coatings used herein were known in the art of mechanical bearings, having been originally taught by Watson in U.S. Pat. No. 2,987,352. Davidson, in U.S. Pat. No. 5,037,428, first taught the application of this form of oxidized zirconium to prosthetic devices.

Importantly, the base materials upon which the oxidized zirconium coating is formed need not be fabricated totally of zirconium or zirconium alloy. The only requirement for the formation of an oxidized zirconium surface is zirconium or zirconium alloy material in the surface before the formation of the oxidized zirconium layer. Upon formation of the oxidized zirconium surface the former surface becomes the first substrate layer. For example, composite materials are possible embodiments of the present invention. This allows one to realize strength and weight advantages of prostheses having one or more different core materials. For example, a synthetic core material having high strength and being of light weight and having a zirconium or zirconium alloy veneer or outer layer is envisioned by the present invention. The interior of the base material may be of one or more than one material, allowing for varying degrees of heterogeneity in the overall fabrication, depending upon the application. Alternatively, a lesser degree of heterogeneity is possible. For example, a base material being relatively rich in zirconium or zirconium alloy at the surface and exhibiting a continuously decreasing zirconium content as a depth into the substrate increases is another possibility. In this latter example, no abrupt macroscopic phase boundary exists within the base material. These examples are meant to be merely illustrative and not exhaustive; variations in the possible embodiments which would be apparent to one of ordinary skill in the art upon a reading of this disclosure are part of the present invention.

The XLPE useful in the present invention is polyethylene cross-linked by any means, irradiative or chemical being illustrative examples which are generally known in the art. Illustrative examples of the prosthetic devices for which the contact interfaces disclosed herein find use are shown in the schematic diagrams, FIGS. 1–4.

A typical hip joint assembly is shown in situ in FIG. 1 and FIG. 2. The hip joint stem 2 fits into the femur while the femoral head 6 of the prosthesis fits into and articulates against the inner lining 8 of an acetabular cup 10 which in turn is affixed to the pelvis as shown in FIG. 1. A porous metal bead or wire mesh coating 12 may be incorporated to allow stabilization of the implant by in-growth of surrounding tissue into the porous coating. Similarly, such a coating can also be applied to the acetabular component. The femoral head 6 may be an integral part of the hip joint stem 2 or may be a separate component mounted upon a conical taper at the end of the neck 4 of the hip joint prosthesis. This allows the fabrication of a prosthesis having a metallic stem and neck but a femoral head of a different material.

This method of construction is often desirable because the use of composite materials allows for the localized optimization of a variety of parameters such as weight, strength and wear resistance. Regardless of the materials, however, the femoral head articulates against the inner surface of the acetabular cup thereby causing wear and, in the long term, this may necessitate prosthesis replacement. This is especially the case where the femoral head is of metal and the acetabular cup is lined with an organic polymer or composite thereof. While these polymeric surfaces provide good, relatively low friction surfaces and are biocompatible, they are, as explained above, subject to wear and accelerated creep due to the frictional heat and torque to which they are subjected during ordinary use.

In the present invention, the inner lining 8 is preferably formed of XLPE and the femoral head 6 is coated with a surface of blue-black or black oxidized zirconium. Preferably, the oxidized zirconium surface coating is 1–20 μm thick, but may be outside this range. It may alternatively be from about 1–5 μm thick. The wire mesh or metal bead surface 12 may be at least partially coated with a surface of blue-black or black oxidized zirconium to promote in-growth of tissue or bone into the device, thereby stabilizing its position.

A typical knee joint prosthesis is shown in situ in FIG. 3 and FIG. 4. The knee joint includes a femoral component 20 and a tibial component 30. The femoral component includes condyles 22 which provide the articulating surface of the femoral component and pegs 24 for affixing the femoral component to the femur. The tibial component 30 includes a tibial base 32 with a peg 34 for mounting the tibial base onto the tibia. A tibial platform 36 is mounted atop the tibial base 32 and is supplied with grooves 38 similar to the shape of the condyles 22. The bottom surfaces of the condyles 26 contact the tibial platform's grooves 38 so that the condyles articulate within these grooves against the tibial platform. In the present invention, the condyles 22 are coated with a surface of blue-black or black oxidized zirconium and the grooves 38 on the tibial platform 36 are comprised of XLPE. Part or all of the remainder of the femoral component 20 and a tibial component 30 may have a surface coating of blue-black or black oxidized zirconium. Preferably, the surface coatings are 1–20 μm thick, but may be outside this range. They may alternatively be from about 1–5 μm thick. As in the case of the hip joint, porous bead or wire mesh coatings can also be applied to either the tibial or femoral components of the knee or both. These porous bead or wire mesh coatings of the knee prosthesis may also be at least partially coated with a surface of blue-black or black oxidized zirconium to promote in-growth of tissue or bone into the device, thereby stabilizing its position.

The base (i.e., substrate) zirconium containing metal alloys are cast or machined by conventional methods to the shape and size desired to obtain a prosthesis substrate. The substrate is then subjected to process conditions which cause the natural (in situ) formation of a tightly adhered, diffusion-bonded coating of oxidized zirconium on its surface. The process conditions include, for instance, air, steam, or water oxidation or oxidation in a salt bath. These processes ideally provide a thin, hard, dense, blue-black or black, low-friction wear-resistant oxidized zirconium film or coating of thickness typically on the order of several microns ($10^{-6}$ meters) on the surface of the prosthesis substrate. Below this coating, diffused oxygen from the oxidation process increases the hardness and strength of the underlying substrate metal.

Importantly, the base materials need not be formed totally of zirconium or zirconium alloy. The only requirement for the formation of an oxidized zirconium surface is that zirconium or zirconium alloy material comprises the surface layer of the base material before the formation of the oxidized zirconium layer. For example, composite materials are possible embodiments of the present invention. This allows one to realize strength and weight advantages of prostheses having one or more different core materials. For example, a synthetic core material having high strength and being of light weight surrounded by a zirconium or zirconium alloy veneer or outer layer is a possible embodiment of the present invention. One or more substrata may comprise the base material and these substrata may be comprised of any suitable material which may or may not include zirconium or zirconium alloy. Alternatively, the base material may consist of a continuous phase in which the concentration of zirconium or zirconium alloy varies with depth into the base material. For example, the surface at which the coating of oxidized zirconium is formed may be relatively rich in zirconium, with this concentration falling off as the distance into the base material (i.e., away from the surface) increases. Variations on the general embodiment are within the scope of the present invention in light of the disclosure.

Representative methods for the formation of the surface coating of blue-black or black oxidized zirconium have been described previously in U.S. Pat. No. 2,987,352 to Watson and U.S. Pat. No. 5,037,428 to Davidson, which are incorporated by reference as though fully set forth herein. A coating thickness of 1 to 5 μm is preferred. Conditions useful for the fabrication of surfaces of varying thickness are described in U.S. Pat. No. 5,037,428. Methods for controlling the uniformity of the oxidized zirconium coating are described in the commonly-assigned copending application Ser. No. 09/381,217, which is incorporated by reference as though fully set forth herein.

Oxygen, niobium, and titanium are common alloying elements in the alloy with oftentimes the presence of hafnium. While such zirconium containing alloys may be custom formulated by conventional methods known in the art of metallurgy, a number of suitable alloys are commercially available. Illustrative examples of these commercial alloys include among others Zircadyne 705, Zircadyne 702, and Zircalloy.

These diffusion-bonded, low friction, highly wear resistant oxidized zirconium coatings are applied to one of the contacting surfaces of orthopedic implants subject to conditions of wear. Such surfaces include the articulating surfaces of knee joints, elbows and hip joints. In the case of hip joints, the femoral head and stem are typically fabricated of metal alloys while the acetabular cup may be fabricated from ceramics. The only requirement is that the surface of the base material of the contacting surface of the device must be of zirconium or zirconium alloy such that upon surface oxidation under the appropriate conditions, measurable surface concentrations of oxidized zirconium are formed. Substrate layers extending into the interior of the base material may consist of one or more materials, any, or, or none of which may be of zirconium or zirconium alloy.

The wear advantages of XLPE over conventional polyethylene are diminished under certain conditions. For instance as the roughness of the counter bearing surface increases, XLPE approaches conventional polyethylene in its wear resistance (See, e.g., McKellop et al., "Wear of Gamma-Crosslinked Polyethylene Acetabular Cups Against Roughened Femoral Balls", *Clin. Orthop.*, (1999) 369, pp. 73–82). The wear advantage of XLPE over conventional polyethylene enhanced by using a low roughness, abrasion resistant articulating surfaces against the XLPE.

There is anecdotal evidence that cross-linked polyethylene is more prone to creep than conventional polyethylene. Thus, there is a potential trade-off to be made in gaining the superior wear characteristics of XLPE over conventional PE in medical implants. However, the articulating bearing surfaces unexpectedly diminished this disadvantage. Creep is a relatively slow plastic deformation process which is more prominent at higher temperatures as a material more closely approaches its melting point. (See "Metallurgy Fundamentals", D. A. Brandt and J. C. Warner, Goodheart-Wilcox Pub. Co., Inc., p. 57, 1999). A contacting surface that is a thermal conductor will diminish the creep resistance advantage of conventional polyethylene over XLPE through its ability to pass heat and avoid a localized rise in temperature. As the temperature of either polymer rises, its ability to withstand protracted stress-strain loads decreases, such that prostheses made of either conventional polyethylene or XLPE are subject to failure. At temperatures significantly lower than the melting point, the two polymers more closely approach one another in their creep resistance.

Oxidized zirconium, is unique with respect to the excellent thermal conductivity it possesses relative to other conventional prosthetic materials. It combines excellent surface roughness characteristics with very high thermal conductivity. In this way, it possesses the relevant beneficial characteristics (in terms of XLPE) of metal and ceramics while avoiding the relevant disadvantages of the former and outperforming the latter. Thus, while all abrasion resistant surfaces such as zirconia and alumina would enjoy the benefit of reduced wear of XLPE and at least some improvement in creep resistance, oxidized zirconium would enjoy both a significant reduced wear and a significant reduced creep susceptibility. Table 1 below schematically illustrates these characteristics.

TABLE 1

Relative Performance of Various Prostheses Surfaces with Respect to Various Characteristics and Overall Degradative Effects on Counter Bearing Surfaces

| | OXIDIZED ZIRCONIUM | ZIRCONIA | ALUMINA | METAL |
|---|---|---|---|---|
| Surface Roughness | 3 | 2 | 2 | 1 |
| Strength | 3 | 1 | 0 | 3 |
| Wear (of itself) | 2 | 2 | 3 | 0 |
| Thermal Conductivity | 3 | 0 | 3 | 3 |
| Wear and Creep of Polyethylene | 2 | 2 | 2 | 0 |
| Wear and Creep of XLPE | 3 | 2 | 2 | 0 |

3 = Excellent
2 = Good
1 = Fair
0 = Poor

The prostheses of the instant invention exhibit design advantages in a variety of applications. Importantly, the wear resistance characteristics of XLPE, already superior relative to UHMWPE is fully realized while the creep characteristics are improved when XLPE articulates against abrasion resistant surfaces. These improvements are further enhanced when XLPE articulates against oxidized zirconium, allowing for the polymer lining to be constructed of lower thickness than in conventional prostheses. The superiority of oxidized zirconium counter bearing surfaces in terms of low friction and high thermal conductivity allows for polymer linings that are thinner still. The synergistic result is a potentially smaller prosthesis having weight advantages over conventional prostheses, which requires less bone resection, greater conformity and contact area, and exhibits reductions in contact stress, an increase in range of motion, and a decreased chance of dislocation. A smaller amount of polymer material is expected to result in a lower likelihood of osteolysis (resulting from a lesser likelihood of material migration) while having the same or greater component service life. Decreases in mass of the prosthesis is expected to be of greater significance in hip applications which are typically larger than knee prostheses and have a smaller range of motion.

The present invention is also useful in knee prostheses. Knee prostheses typically are of two varieties: mobile bearing knees (MBK) and fixed bearing knees (FBK). Referring to FIGS. 3 and 4, the MBK is characterized by having its articulating tibial component 30 movable relative to the tibial platform 36. This results in wear and creep on both the top and bottom of the tibial component 30. In contrast, this interface in the FBK is fixed and the only movement is between the top of the tibial component and the condyles 22. As a result, the MBK has a greater range of motion but suffers from greater wear and creep than an FBK. XLPE generally offers greater wear and comparable creep resistance over UHMWPE when articulating against abrasion resistant surfaces. This characteristic is enhanced where the tibial tray is formed of oxidized zirconium. This same advantage is also seen in FBK prostheses, but is limited to the articulating interface between the tibial component 30 and the condyles 22.

Zirconium or zirconium alloy can also be used to provide a porous bead or wire mesh surface to which surrounding bone or other tissue may integrate to stabilize the oxidized zirconium-on-oxidized zirconium prosthesis. These porous coatings can be treated simultaneously by the oxidation treatment in a manner similar to the oxidation of the base prosthesis for the elimination or reduction of metal ion release. Furthermore, zirconium or zirconium alloy can also be used as a surface layer applied over conventional implant materials prior to in situ oxidation and formation of the oxidized zirconium coating.

Although the invention has been described with reference to its preferred embodiments, those of ordinary skill in the art may, upon reading this disclosure, appreciate changes and modifications which may be made and which do not depart from the scope and spirit of the invention as described above or claimed hereafter.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

| U.S. Pat. No. 5,037,438 | August 1991 | Davidson |
| U.S. Pat. No. 4,145,746 | March 1979 | Suzuki et al. |
| U.S. Pat. No. 3,677,795 | July 1972 | Bokros et al. |
| U.S. Pat. No. 2,987,352 | February 1958 | Watson |
| U.S. Pat. No. 4,671,824 | June 1987 | Haygarth |
| U.S. App. S/N 09/381,217 | filed November 1999 | Hunter et al. |

Hunter, G. et al., *Mat. Res. Soc. Symp. Proc.,* 1999, 550, 337.

McKellop et al., "Wear of Gamma-Crosslinked Polyethylene Acetabular Cups Against Roughened Femoral Balls", *Clin. Orthop.,* (1999) 369, pp. 73–82.

Hunter et al., "Abrasive Wear of Oxidized Zr-2.5Nb, CoCrMo, and Ti-6Al-4V Against Bone Cement", *6th World Biomaterials Cong. Trans., Society for Biomaterials,* Minneapolis, Minn., (2000), p. 835

What is claimed is:

1. A prosthesis for implantation in a patient, comprising:
   (a) a prosthesis body comprising zirconium or zirconium alloy, said prosthesis body comprising an implant portion for inserting into the body tissue of the patient;
   (b) a bearing surface comprising at least one condyle on the prosthesis body;
   (c) a tibial component comprising cross-linked polyethylene having a surface adapted to cooperate with the bearing surface; and,
   (d) a thin coating of blue-black or black oxidized zirconium directly on the bearing surface of the condyle portion.

2. The prosthesis of claim 1 wherein said thin blue-black or black oxidized zirconium coating is from about 1 to about 20 microns thick.

3. The prosthesis of claim 1 wherein said thin blue-black or black oxidized zirconium coating is from about 1 to about 5 microns thick.

4. The prosthesis of claim 1 wherein the implant portion of the prosthesis body further comprises an irregular surface structure adapted to accommodate tissue in-growth on a portion of the prosthesis body.

5. The prosthesis of claim 4 wherein the irregular surface structure comprises zirconium or zirconium alloy beads attached to the outer surface of the prosthesis body, wherein at least a portion of the surface of the beads is oxidized to blue-black or black oxidized zirconium.

6. The prosthesis of claim 4 wherein the irregular surface structure comprises zirconium or zirconium alloy wire mesh connected to the outer surface of the prosthesis body, wherein at least a portion of the surface of the mesh is oxidized to blue-black or black oxidized zirconium.

7. The prosthesis of claim 1 wherein the prosthesis body further comprises at least one substrate layer.

8. The prosthesis of claim 1 wherein the prosthesis body further comprises at least one substrate layer having a depth-dependent variable concentration of zirconium.

9. A prosthesis for implantation in a patient, comprising:
   (a) a hip prosthesis body for implantation into a femur comprising a head portion, said head portion comprising zirconium or zirconium alloy;
   (b) a bearing surface on the head portion of the prosthesis body;
   (c) an acetabular cup having an inner surface comprising cross-linked polyethylene, said inner surface being adapted to cooperate with the bearing surface on the head portion; and,
   (d) a thin coating of blue-black or black oxidized zirconium directly on the bearing surface of the head portion.

10. The prosthesis of claim 9 wherein said thin blue-black or black oxidized zirconium coating is from about 1 to about 20 microns thick.

11. The prosthesis of claim 9 wherein said thin blue-black or black oxidized zirconium coating is from about 1 to about 5 microns thick.

12. The prosthesis of claim 9 wherein the prosthesis body further comprises an irregular surface structure adapted to accommodate tissue in-growth on a portion of the prosthesis body.

13. The prosthesis of claim 12 wherein the irregular surface structure comprises zirconium or zirconium alloy beads connected to the outer surface of the prosthesis body, wherein at least a portion of the surface of the beads is oxidized to blue-black or black oxidized zirconium.

14. The prosthesis of claim 12 wherein the irregular surface structure comprises zirconium or zirconium alloy wire mesh connected to the outer surface of the prosthesis body, wherein at least a portion of the surface of the mesh is oxidized to blue-black or black oxidized zirconium.

15. The prosthesis of claim 9 wherein the hip prosthesis body further comprises at least one substrate layer.

16. The prosthesis of claim 9 wherein the hip prosthesis body further comprises at least one substrate layer having a depth-dependent variable concentration of zirconium.

17. A prosthesis for implantation in a patient, comprising a first prosthesis portion and a second prosthesis portion;
   (a) said first prosthesis portion comprising zirconium or zirconium alloy, said prosthesis body comprising an implant portion for insertion into the body tissue of the patient;
   (b) a bearing surface on the first prosthesis portion, the bearing surface being sized and shaped to engage or cooperate with a second bearing surface on said second prosthesis portion, said second bearing surface comprising cross-linked polyethylene; and,
   (c) a coating of blue-black or black oxidized zirconium from about 1 to about 5 microns in thickness on the bearing surface of the first prosthesis portion.

18. The prosthesis of claim 17 wherein the first prosthesis portion is a hip joint having a head portion as a bearing surface and wherein said another prosthesis portion is an acetabular cup, said head portion being adapted to cooperate with the inner surface of the acetabular cup, wherein said inner surface of said acetabular cup is also said second bearing surface.

19. The prosthesis of claim 17 wherein the first prosthesis portion is a knee joint and the bearing surface of the prosthesis body comprises at least one condyle, and wherein said another prosthesis portion comprises a tibial component, said at least one condyle being adapted to cooperate with said tibial component.

20. The prosthesis of claim 17 wherein the first prosthesis portion further comprises an irregular surface structure adapted to accommodate tissue in-growth on at least a portion of the prosthesis body.

21. The prosthesis of claim 20 wherein the irregular surface structure comprises zirconium or zirconium alloy beads connected to the outer surface of the first prosthesis portion, wherein at least a portion of the surface of the beads is oxidized to blue-black or black oxidized zirconium.

22. The prosthesis of claim 20 wherein the irregular surface structure comprises zirconium or zirconium alloy wire mesh connected to the outer surface of the first prosthesis portion, wherein at least a portion of the surface of the mesh is oxidized to blue-black or black oxidized zirconium.

23. The prosthesis of claim 17 wherein the first prosthesis portion further comprises at least one substrate layer.

24. The prosthesis of claim 17 wherein the first prosthesis portion further comprises at least one substrate layer having a depth-dependent variable concentration of zirconium.

25. A prosthesis for implantation in a patient, comprising:
(a) a prosthesis body comprising zirconium or zirconium alloy, said prosthesis body comprising an implant portion for inserting into the body tissue of the patient;
(b) a bearing surface on the prosthesis body;
(c) a counter-bearing surface comprising cross-linked polyethylene and adapted to cooperate with the bearing surface; and,
(d) a thin coating of blue-black or black oxidized zirconium directly on the bearing surface.

26. The prosthesis of claim 25 wherein said thin blue-black or black oxidized zirconium coating is from about 1 to about 20 microns thick.

27. The prosthesis of claim 25 wherein said thin blue-black or black oxidized zirconium coating is from about 1 to about 5 microns thick.

28. The prosthesis of claim 25 wherein the implant portion of the prosthesis body further comprises an irregular surface structure adapted to accommodate tissue in-growth on a portion of the prosthesis body.

29. The prosthesis of claim 28 wherein the irregular surface structure comprises zirconium or zirconium alloy beads attached to the outer surface of the prosthesis body, wherein at least a portion of the surface of the beads is oxidized to blue-black or black oxidized zirconium.

30. The prosthesis of claim 28 wherein the irregular surface structure comprises zirconium or zirconium alloy wire mesh connected to the outer surface of the prosthesis body, wherein at least a portion of the surface of the mesh is oxidized to blue-black or black oxidized zirconium.

31. The prosthesis of claim 25 wherein the prosthesis body further comprises at least one substrate layer.

32. The prosthesis of claim 25 wherein the prosthesis body further comprises at least one substrate layer having a depth-dependent variable concentration of zirconium.

33. A prosthesis for implantation in a patient, comprising:
(a) a prosthesis body comprising a substrate material, said prosthesis body comprising an implant portion for inserting into the body tissue of the patient;
(b) a bearing surface on the prosthesis body comprised of a ceramic material; and,
(c) a counter-bearing surface comprising cross-linked polyethylene and adapted to cooperate with the bearing surface.

34. The prosthesis of claim 33 wherein said ceramic material is selected from the group consisting of zirconia and alumina.

* * * * *